United States Patent
Choy et al.

(10) Patent No.: US 9,840,476 B2
(45) Date of Patent: Dec. 12, 2017

(54) 5-FLUORO-4-IMINO-3-(ALKYL/ SUBSTITUTED ALKYL)-1- (ARYLSULFONYL)-3,4- DIHYDROPYRIMIDIN-2(1H)-ONE AND PROCESSES FOR THEIR PREPARATION

(71) Applicant: Adama Makhteshim Ltd., Airport (IL)

(72) Inventors: Nakyen Choy, Carmel, IN (US); Ronald Ross, Jr., Zionsville, IN (US)

(73) Assignee: ADAMA MAKTESHIM LTD., Airport (IL)

( * ) Notice: Subject to any disclaimer, the term of this patent is extended or adjusted under 35 U.S.C. 154(b) by 0 days.

(21) Appl. No.: 15/173,529

(22) Filed: Jun. 3, 2016

(65) Prior Publication Data

US 2016/0280663 A1  Sep. 29, 2016

Related U.S. Application Data

(63) Continuation of application No. 14/584,368, filed on Dec. 29, 2014, now abandoned.

(60) Provisional application No. 61/922,572, filed on Dec. 31, 2013, provisional application No. 61/922,582, filed on Dec. 31, 2013.

(51) Int. Cl.
*C07D 239/10* (2006.01)
*C07D 239/22* (2006.01)
*C07D 239/47* (2006.01)
*A01N 43/54* (2006.01)

(52) U.S. Cl.
CPC ........... *C07D 239/47* (2013.01); *A01N 43/54* (2013.01)

(58) Field of Classification Search
CPC ............................ C07D 239/10; C07D 239/22
See application file for complete search history.

(56) References Cited

U.S. PATENT DOCUMENTS

| | | | |
|---|---|---|---|
| 3,309,359 A | 3/1967 | Duschinsky et al. |
| 3,368,938 A | 2/1968 | Berger et al. |
| 3,635,977 A | 1/1972 | Lutz et al. |
| 3,868,373 A | 2/1975 | Hoffer |
| 4,009,272 A | 2/1977 | Konig et al. |
| 4,845,081 A | 7/1989 | Sloan |
| 4,996,208 A | 2/1991 | Lindner et al. |
| 5,962,489 A | 10/1999 | Mueller et al. |
| 6,066,638 A | 5/2000 | Bereznak et al. |
| 6,617,330 B2 | 9/2003 | Walter |
| 7,914,799 B2 | 3/2011 | Patashnik et al. |
| 8,263,603 B2 | 9/2012 | Boebel et al. |
| 8,318,758 B2 | 11/2012 | Boebel et al. |
| 8,470,839 B2 | 6/2013 | Boebel et al. |
| 8,552,020 B2 | 10/2013 | Pobanz et al. |
| 8,658,660 B2 | 2/2014 | Boebel et al. |
| 8,916,579 B2 | 12/2014 | Boebel et al. |
| 9,000,002 B2 | 4/2015 | Pobanz et al. |
| 9,006,259 B2 | 4/2015 | Webster et al. |
| 9,271,497 B2 | 3/2016 | Lorsbach et al. |
| 9,321,734 B2 | 4/2016 | Lorsbach et al. |
| 9,526,245 B2 | 12/2016 | Owen et al. |
| 9,532,570 B2 | 1/2017 | Owen et al. |
| 9,538,753 B2 | 1/2017 | Owen et al. |
| 2003/0039667 A1 | 2/2003 | Jira et al. |
| 2008/0004253 A1 | 1/2008 | Branstetter et al. |
| 2008/0269238 A1 | 10/2008 | Sugihara et al. |
| 2009/0203647 A1 | 8/2009 | Benko et al. |
| 2009/0269238 A1 | 8/2009 | Benko et al. |
| 2010/0022538 A1 | 1/2010 | Boebel et al. |
| 2010/0029482 A1 | 2/2010 | Benko et al. |
| 2010/0029483 A1 | 2/2010 | Iskandar et al. |
| 2011/0034490 A1 | 2/2011 | Boebel et al. |
| 2011/0034491 A1 | 2/2011 | Boebel et al. |
| 2011/0034492 A1 | 2/2011 | Schipper et al. |
| 2011/0034493 A1 | 2/2011 | Boebel et al. |
| 2011/0053891 A1 | 3/2011 | Boebel et al. |
| 2011/0263627 A1 | 10/2011 | Boebel et al. |
| 2013/0045984 A1 | 2/2013 | Boebel et al. |
| 2014/0011824 A1 | 1/2014 | Pobanz et al. |

(Continued)

FOREIGN PATENT DOCUMENTS

| | | |
|---|---|---|
| EP | 0102908 | 3/1984 |
| EP | 0139613 | 5/1985 |
| EP | 0332579 | 9/1989 |
| EP | 0877022 | 4/2003 |
| EP | 1952689 | 8/2008 |

(Continued)

OTHER PUBLICATIONS

International Preliminary Report on Patentability dated Jul. 5, 2016 in connection with PCT/US2014/072569 (WO 2015/103144), filed Dec. 29, 2014.
PCT International Search Report dated Sep. 21, 2010 in connection with PCT/US2010/044579 (WO 2011/017540), filed Aug. 5, 2010.
PCT International Search Report dated Sep. 21, 2010 in connection with PCT/US2010/044592 (WO 2011/017547), filed Aug. 5, 2010.
PCT International Search Report dated Sep. 23, 2010 in connection with PCT/US2010/044576 (WO 2011/017538), filed Aug. 5, 2010.

(Continued)

*Primary Examiner* — Bruck Kifle
(74) *Attorney, Agent, or Firm* — Gary J. Gershik; Cooper & Dunham LLP

(57) ABSTRACT

Provided herein are 5-fluoro-4-imino-3-(alkyl/substituted alkyl)-1-(arylsulfonyl)3,4-dihydropyrimidin-2(1H)-one and processes for their preparation which may include the use of an alkali alkoxide and an alkylating agent

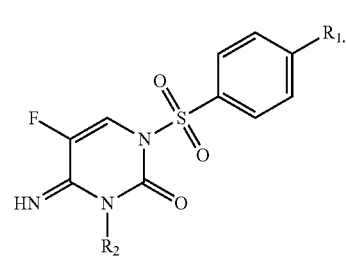

20 Claims, No Drawings

(56) References Cited

U.S. PATENT DOCUMENTS

| | | |
|---|---|---|
| 2015/0111851 A1 | 4/2015 | Boebel et al. |
| 2015/0191436 A1 | 4/2015 | Webster et al. |
| 2015/0181874 A1 | 7/2015 | Lorsbach et al. |
| 2015/0181875 A1 | 7/2015 | Owen et al. |
| 2015/0181883 A1 | 7/2015 | Lorsbach et al. |
| 2015/0183749 A1 | 7/2015 | Choy, Jr. |
| 2015/0183750 A1 | 7/2015 | Choy, Jr. |
| 2015/0342188 A1 | 12/2015 | Lorsbach et al. |
| 2015/0353506 A1 | 12/2015 | Lorsbach et al. |
| 2015/0359225 A1 | 12/2015 | Lorsbach et al. |
| 2016/0192653 A1 | 7/2016 | Lorsbach et al. |
| 2016/0198711 A1 | 7/2016 | Lorsbach et al. |
| 2016/0280662 A1 | 9/2016 | Choy et al. |
| 2017/0008855 A1 | 1/2017 | Boebel et al. |

FOREIGN PATENT DOCUMENTS

| | | |
|---|---|---|
| GB | 1461184 | 1/1977 |
| JP | 061793 | 1/1994 |
| JP | 2002-530409 | 9/2002 |
| JP | 2013-501728 | 8/2010 |
| JP | 2012-502905 | 2/2012 |
| NZ | 597644 | 9/2014 |
| WO | 97/33890 | 9/1997 |
| WO | WO 97/33890 | 9/1997 |
| WO | 02/30922 | 4/2002 |
| WO | WO 02/30922 | 4/2002 |
| WO | 2008/083465 | 7/2008 |
| WO | WO 2008/083465 | 7/2008 |
| WO | 2009/094442 | 7/2009 |
| WO | WO 2009/094442 | 7/2009 |
| WO | 2010/047866 | 4/2010 |
| WO | WO 2010/047866 | 4/2010 |
| WO | 2010/085377 | 7/2010 |
| WO | WO 2010/085377 | 7/2010 |
| WO | WO 2011/017538 A1 | 2/2011 |
| WO | WO 2011/017540 A1 | 2/2011 |
| WO | WO 2011/017544 A1 | 2/2011 |
| WO | WO 2011/017545 A1 | 2/2011 |
| WO | WO 2011/017547 A1 | 2/2011 |
| WO | WO 2011/043876 A1 | 4/2011 |
| WO | WO 2011/137002 A1 | 11/2011 |
| WO | WO 2013/025795 A1 | 2/2013 |
| WO | WO 2014/105821 A1 | 7/2014 |
| WO | WO 2014/105841 A1 | 7/2014 |
| WO | WO 2014/105844 A1 | 7/2014 |
| WO | WO 2014/105845 A1 | 7/2014 |
| WO | WO 2015/103142 A1 | 7/2015 |
| WO | WO 2015/103144 A1 | 7/2015 |
| WO | WO 2015/103259 A1 | 7/2015 |
| WO | WO 2015/103261 A1 | 7/2015 |
| WO | WO 2015/103262 A1 | 7/2015 |

OTHER PUBLICATIONS

PCT International Search Report dated Jul. 5, 2011 in connection with PCT/US2011/033203 (WO 2011/137002), filed Apr. 20, 2011.
Written Opinion of the International Searching Authority dated Jul. 5, 2011 in connection with PCT/US2011/033203 (WO 2011/137002), filed Apr. 20, 2011.
International Preliminary Report on Patentability dated Oct. 30, 2012 in connection with PCT/US2011/033203 (WO 2011/137002), filed Apr. 20, 2011.
PCT International Search Report dated Oct. 15, 2012 in connection with PCT/US2012/050930 (WO 2013/025795), filed Aug. 15, 2012.
Written Opinion of the International Searching Authority dated Oct. 15, 2012 in connection with PCT/US2012/050930 (WO 2013/025795), filed Aug. 15, 2012.
International Preliminary Report on Patentability dated Feb. 18, 2014 in connection with PCT/US2012/050930 (WO 2013/025795), filed Aug. 15, 2012.
PCT International Search Report dated Apr. 28, 2015 in connection with PCT/US2014/072745 (WO 2015/103259), filed Dec. 30, 2014.
International Preliminary Report on Patentability dated Jul. 5, 2016 in connection with PCT/US2014/072745 (WO 2015/103259), filed Dec. 30, 2014.
Written Opinion of the International Searching Authority dated Apr. 28, 2015 in connection with PCT/US2014/072745 (WO 2015/103259), filed Dec. 30, 2014.
PCT International Search Report dated Apr. 29, 2015 in connection with PCT/US2014/072747 (WO 2015/103261), filed Dec. 30, 2014.
International Preliminary Report on Patentability dated Jul. 5, 2016 in connection with PCT/US2014/072747 (WO 2015/103261), filed Dec. 30, 2014.
Written Opinion of the International Searching Authority dated Apr. 29, 2015 in connection with PCT/US2014/072747 (WO 2015/103261), filed Dec. 30, 2014.
PCT International Search Report dated May 21, 2015 in connection with PCT/US2014/072748 (WO 2015/103262), filed Dec. 30, 2014.
International Preliminary Report on Patentability dated Jul. 5, 2016 in connection with PCT/US2014/072748 (WO 2015/103262), filed Dec. 30, 2014.
Written Opinion of the International Searching Authority dated May 21, 2015 in connection with PCT/US2014/072748 (WO 2015/103262), filed Dec. 30, 2014.
PCT International Search Report dated Jan. 22, 2009 in connection with PCT International Application No. PCT/US/2009/031683 (WO 2009/094442), filed Jan. 22, 2009.
PCT International Search Report dated Mar. 14, 2011 in connection with PCT/US/2011/020351 (WO 2011/085084), filed Jan. 6, 2011.
PCT International Search Report dated Oct. 1, 2010 in connection with PCT/US/2010/044588 (WO 2011/017545), filed Aug. 5, 2010.
PCT International Search Report dated Oct. 9, 2010 in connection with PCT International Application No. PCT/US/2012/050931 (WO 2013/025796), filed Aug. 15, 2012.
PCT International Search Report dated Apr. 22, 2011 in connection with PCT/US/2010/060792 (WO 2011/084611), filed Dec. 16, 2010.
Nov. 10, 2011 Non-Final Office Action issued by the U.S. Patent and Trademark Office in connection with U.S. Appl. No. 13/090,616.
Feb. 9, 2012 Response to Nov. 10, 2011 Non-Final Office Action issued by the U.S. Patent and Trademark Office in connection with U.S. Appl. No. 13/090,616.
May 14, 2013 Non-Final Office Action issued by the U.S. Patent and Trademark Office in connection with U.S. Appl. No. 13/586,450.
Aug. 14, 2013 Response to May 14, 2013 Non-Final Office Action issued by the U.S. Patent and Trademark Office in connection with U.S. Appl. No. 13/586,450.
Mar. 4, 2015 Non-Final Office Action issued by the U.S. Patent and Trademark Office in connection with U.S. Appl. No. 14/584,347.
Jun. 4, 2015 Response to Mar. 4, 2015 Non-Final Office Action issued by the U.S. Patent and Trademark Office in connection with U.S. Appl. No. 14/584,347.
Jul. 2, 2015 Final Office Action issued by the U.S. Patent and Trademark Office in connection with U.S. Appl. No. 14/584,347.
Sep. 2, 2015 Response to Jul. 2, 2015 Final Office Action issued by the U.S. Patent and Trademark Office in connection with U.S. Appl. No. 14/584,347.
Sep. 9, 2015 Advisory Action issued by the U.S. Patent and Trademark Office in connection with U.S. Appl. No. 14/584,347.
Nov. 23, 2016 Office Action issued by the U.S. Patent and Trademark Office in connection with U.S. Appl. No. 15/173,493.
Mar. 5, 2015 Non-Final Office Action issued by the U.S. Patent and Trademark Office in connection with U.S. Appl. No. 14/584,368.
Jun. 4, 2015 Response to Mar. 5, 2015 Non-Final Office Action issued by the U.S. Patent and Trademark Office in connection with U.S. Appl. No. 14/584,368.
Jul. 2, 2015 Final Office Action issued by the U.S. Patent and Trademark Office in connection with U.S. Appl. No. 14/584,368.
Sep. 2, 2015 Response to Jul. 2, 2015 Final Office Action issued by the U.S. Patent and Trademark Office in connection with U.S. Appl. No. 14/584,368.
Sep. 10, 2015 Advisory Action issued by the U.S. Patent and Trademark Office in connection with U.S. Appl. No. 14/584,368.
Dec. 1, 2016 Office Action issued by the U.S. Patent and Trademark Office in connection with U.S. Appl. No. 15/173,529.

(56) References Cited

OTHER PUBLICATIONS

Dec. 18, 2015 Non-Final Office Action issued by the U.S. Patent and Trademark Office in connection with U.S. Appl. No. 14/585,945.
Mar. 16, 2016 Response to Dec. 18, 2015 Non-Final Office Action issued by the U.S. Patent and Trademark Office in connection with U.S. Appl. No. 14/585,945.
Apr. 11, 2016 Final Office Action issued by the U.S. Patent and Trademark Office in connection with U.S. Appl. No. 14/585,945.
Aug. 11, 2016 Response to Apr. 11, 2016 Final Office Action issued by the U.S. Patent and Trademark Office in connection with U.S. Appl. No. 14/585,945.
Dec. 18, 2015 Non-Final Office Action issued by the U.S. Patent and Trademark Office in connection with U.S. Appl. No. 14/585,952.
Mar. 16, 2016 Response to Dec. 18, 2015 Non-Final Office Action issued by the U.S. Patent and Trademark Office in connection with U.S. Appl. No. 14/585,952.
Apr. 12, 2016 Final Office Action issued by the U.S. Patent and Trademark Office in connection with U.S. Appl. No. 14/585,952.
Aug. 11, 2016 Response to Apr. 12, 2016 Final Office Action issued by the U.S. Patent and Trademark Office in connection with U.S. Appl. No. 14/585,952.
Dec. 18, 2015 Non-Final Office Action issued by the U.S. Patent and Trademark Office in connection with U.S. Appl. No. 14/585,962.
Mar. 16, 2016 Response to Dec. 18, 2015 Non-Final Office Action issued by the U.S. Patent and Trademark Office in connection with U.S. Appl. No. 14/585,962.
Apr. 12, 2016 Final Office Action issued by the U.S. Patent and Trademark Office in connection with U.S. Appl. No. 14/585,962.
Aug. 12, 2016 Response to Apr. 12, 2016 Final Office Action issued by the U.S. Patent and Trademark Office in connection with U.S. Appl. No. 14/585,962.
Oct. 5, 2016 Communication pursuant to Rules 161(2) and 162 EPC issued by the European Patent Office in connection with European Patent Application No. 14877285.8.
Dec. 23, 2016 First Examination Report issued by the Australian Patent Office in connection with Australian Patent Application No. 2014373959.
Aug. 9, 2016 Office Action issued by the Colombian Patent Office in connection with Colombian Patent Application No. NC2016-0000512.
Jul. 14, 2016 Office Action issued by the Cuban Patent Office in connection with Cuban Patent Application No. 2016-0099 (including English language translation).
Oct. 6, 2016 Response to Jul. 14, 2016 Office Action issued by the Cuban Patent Office in connection with Cuban Patent Application No. 2016-0099.
Oct. 5, 2016 Communication pursuant to Rules 161(2) and 162 EPC issued by the European Patent Office in connection with European Patent Application No. 14875976.4.
Dec. 23, 2016 First Examination Report issued by the Australian Patent Office in connection with Australian Patent Application No. 2014373961.
Jan. 12, 2017 First Examination Report issued by the New Zealand Patent Office in connection with New Zealand Patent Application No. 722439.
Jan. 12, 2017 First Examination Report issued by the New Zealand Patent Office in connection with New Zealand Patent Application No. 722438.
Jun. 24, 2013 Supplemental European Search Report issued by the EPO in connection with European Patent Application No. 11775446.5, filed Apr. 20, 2011.
Sep. 25, 2014 Communication pursuant to Article 94(3) EPC issued by the European Patent Office in connection with European Patent Application No. 11775446.5-1462.
Feb. 4, 2015 Response to Sep. 25, 2014 Communication pursuant to Article 94(3) EPC issued by the European Patent Office in connection with European Patent Application No. 11775446.5-1462.
European Search Opinion issued by the EPO in connection with European Patent Application No. 11775446.5.
Feb. 3, 2014 Response to European Search Opinion issued by the EPO in connection with European Patent Application No. 11775446.5.
Mar. 23, 2015 Response to Aug. 28, 2014 First Examination Report issued by the Australian Patent Office in connection with Australian Patent Application No. 2011245544.
Jan. 11, 2017 Office Action issued by the Canadian Patent Office in connection with Canadian Patent Application No. 2,797,226.
Aug. 25, 2015 Office Action issued by the Chilean Patent Office in connection with Chilean Patent Application No. 2979-2012.
May 26, 2016 Office Action issued by the Chilean Patent Office in connection with Chilean Patent Application No. 2979-2012.
Aug. 22, 2016 Response to May 26, 2016 Office Action issued by the Chilean Patent Office in connection with Chilean Patent Application No. 2979-2012.
Oct. 17, 2013 Office Action issued by the Chinese Patent Office in connection with Chinese Patent Application No. 201180031680.8.
Feb. 28, 2014 Response to Oct. 17, 2013 Office Action issued by the Chinese Patent Office in connection with Chinese Patent Application No. 201180031680.8.
May 23, 2014 Office Action issued by the Chinese Patent Office in connection with Chinese Patent Application No. 201180031680.8.
Sep. 24, 2013 Office Action issued by the Colombian Patent Office in connection with Colombian Patent Application No. 12213540.
Dec. 18, 2013 Response to Sep. 24, 2013 Office Action issued by the Colombian Patent Office in connection with Colombian Patent Application No. 12213540.
Jun. 22, 2015 Response to Mar. 22, 2015 Office Action issued by the Israeli Patent Office in connection with Israeli Patent Application No. 222646.
Feb. 10, 2015 Office Action issued by the Japanese Patent Office in connection with Japanese Patent Application No. 2013-508042.
May 10, 2015 Response to Feb. 10, 2015 Office Action issued by the Japanese Patent Office in connection with Japanese Patent Application No. 2013-508042.
Jul. 3, 2014 Response to May 26, 2014 Office Action issued by the Mexican Patent Office Mexican Patent Application No. MX/a/2012/012530.
Jun. 14, 2013 First Examination Report issued by the New Zealand Patent Office in connection with New Zealand Patent Application No. 603151.
Oct. 1, 2013 Response to Jun. 14, 2013 First Examination Report issued by the New Zealand Patent Office in connection with New Zealand Patent Application No. 603151.
Jun. 17, 2016 Office Action issued by the Filipino Patent Office in connection with Filipino Patent Application No. 1/2012/502138.
Sep. 28, 2016 Office Action issued by the Filipino Patent Office in connection with Filipino Patent Application No. 1/2012/502138.
Jan. 19, 2015 Office Action issued by the Russian Patent Office in connection with Russian Patent Application No. 2012150293.
Apr. 19, 2015 Response to Jan. 19, 2015 Office Action issued by the Russian Patent Office in connection with Russian Patent Application No. 2012150293.
Apr. 16, 2014 Office Action issued by the Ukrainian Patent Office in connection with Ukrainian Patent Application No. 2012 13412.
Oct. 30, 2014 Response to Apr. 16, 2014 Office Action issued by the Ukrainian Patent Office in connection with Ukrainian Patent Application No. 2012 13412.
Nov. 20, 2016 Response to Jul. 20, 2016 Notice Before Examination issued by the Israeli Patent Office in connection with Israeli Patent Application No. 246511.
Nov. 20, 2016 Response to Jul. 20, 2016 Notice Before Examination issued by the Israeli Patent Office in connection with Israeli Patent Application No. 246512.
Woese et al, (1990) "Towards a natural system of organisms: Proposal for the domains Archaea, Bacteria, and Eucarya." Proc. Acad. Sci., 87:4576-4579.
Jaworski et al. (1990) "Infrared spectra and tautomerism of 5-fluorocytosine, 5-bromocytosine and 5-iodocytosine Matrix isolation and theoretical ab initio studies." J. of Molecular Structure. 223: 63-92 (Abstract).
PCT International Search Report dated Apr. 2, 2015 in connection with PCT/US2014/072569 (WO 2015/103144), filed Dec. 29, 2014.

(56) References Cited

OTHER PUBLICATIONS

Duschinsky et al. (1966) "Nucleosides. XXXIII. N4-Acylated 5-Fluorocytosines and a Direct Synthesis of 5-Fluoro-2'-deoxycytidine" J. of Medicinal Chemistry. 9(4): 566-572.
Lewis et al. (1995)"Synthesis and in vitro anti-human cytomegalovirus (hcmv) activity of certain alkenyl substituted cytosines and 5-halocytosines." J. of Heterocyclic Chemistry. 32 (5): 1513-1515.
Zhang et al. (1989) "Improved method for synthesis of 5-fluorocytosine (5-FC)." CAPLUS Abstract, 111:134074.
PCT International Search Report dated Apr. 8, 2015 in connection with PCT/US2014/072566 (WO 2015/103142), filed Dec. 29, 2014.
International Preliminary Report on Patentability dated Jul. 5, 2016 in connection with PCT/US2014/072566 (WO 2015/103142), filed Dec. 29, 2014.
Written Opinion of the International Searching Authority dated Apr. 8, 2015 in connection with PCT/US2014/072566 (WO 2015/103142), filed Dec. 29, 2014.
PCT International Search Report dated Apr. 2, 2015 in connection with PCT/US2014/072569 (WO 2015/103144), filed 12/29/14.
Written Opinion of the International Searching Authority dated Apr. 2, 2015 in connection with PCT/US2014/072569 (WO 2015/103144), filed Dec. 29, 2014.
Bera et al. (2002) "Nucleosides with furanyl scaffolds." Tetrahedron, Elsevier Science Publishers. 58(24): 4865-4871.
Chiacchio et al. (2003) "Enantioselective Syntheses and Cytotoxicity of N,O-Nucleosides." J. of Medicinal Chemistry, American Chemical Society. 46(1): 3696-3702.
Duschinsky et al. (1966) "Nucleosides. XXXIII. N4-Acylated 5-Fluorocytosines and a Direct Synthesis of 5-Fluoro-2'-deoxycytidine" J. of Medicinal Chemistry. 9(4): 566-572.
Dushinsky et al. (1964) "Cytosine derivatives." CAPLUS Abstract 61:18527.
Gabriella et al. (1963) "Some 5-fluorosulfailamidopyrimidines." Gazzette Chimica Italiana. 93(10): 1268-1278.
Kulikowski et al. (1978) "Methylation and tautomerism of 5-fluorocytosine nucleosides and their analogues." J. Nucleic Acids Research, Special Publication. 4(1): S7-S10.
Lewis et al. (1995)"Synthesis and in vitro anti-human cytomegalovirus (hcmv) activity of certain alkenyl substituted cytosines and 5-halocytosines." J. of Heterocyclic Chemistry. 32(5): 1513-1515.
Liang et al. (2007) "A facile synthesis and herbicidal activities of novel fluorine-containing thiazolo[4,5-d] pyrimidin-7(6H)-ones." J. of Fluorine Chemistry , 128(7): 879-884.
Robins et al. (1972) "A direct synthesis of 5-fluorocytosine and its nucleosides using trifluromethyl hypofluorite." J. of the Chemical Society, Chemical Communications. 1(1): 18.
Waring (2009) "Defining optimum lipophilicity and molecular weight ranges for drug candidates-Molecular weight dependent lower logD limits based on permeability." Bioorganic & Medicinal Chemistry Letters, 19(10): 2844-2851.
Zhang et al. (1989) "Improved method for synthesis of 5-fluorocytosine (5-Fc)." CAPLUS Abstract, 111:134074.

5-FLUORO-4-IMINO-3-(ALKYL/ SUBSTITUTED ALKYL)-1-(ARYLSULFONYL)-3,4-DIHYDROPYRIMIDIN-2(1H)-ONE AND PROCESSES FOR THEIR PREPARATION

CROSS REFERENCE TO RELATED APPLICATIONS

This application is a continuation of U.S. Ser. No. 14/584,368, filed December 29, 2014, which claims the benefit of U.S. Provisional Patent Application Ser. Nos. 61/922,572 and 61/922,582, each filed Dec. 31, 2013, the disclosures of which are expressly incorporated by reference herein.

FIELD

Provided herein are 5-fluoro-4-imino-3-(alkyl/substituted alkyl)1-(arylsulfonyl)-3,4-dihydropyrimidin-2(1H)-one and processes for their preparation.

BACKGROUND AND SUMMARY

U.S. patent application Ser. No. 13/090,616, U.S. Pub. No. 2011/0263627, describes inter alia certain N3-substituted-N1-sulfonyl-5-fluoropyrimidinone compounds and their use as fungicides. The disclosure of the application is expressly incorporated by reference herein. This patent describes various routes to generate N3-substituted-N1-sulfonyl-5-fluoropyrimidinone compounds. It may be advantageous to provide more direct and efficient methods for the preparation, isolation, and purification of N3-substituted-N1-sulfonyl-5-fluoropyrimidinone fungicides and related compounds, e.g., by the use of reagents and/or chemical intermediates and isolation and purification techniques which provide improved time and cost efficiency.

Provided herein are 5-fluoro-4-imino-3-(alkyl/substituted alkyl)-1-(arylsulfonyl)-3,4-dihydropyrimidin-2(1H)-one and processes for their preparation. In one embodiment, provided herein is a process for the preparation of compounds of Formula III:

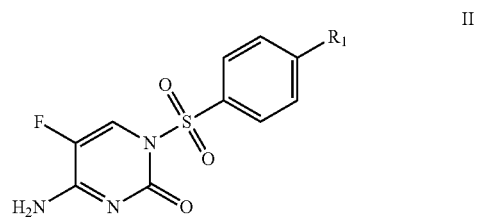

III wherein $R_1$ is selected from:

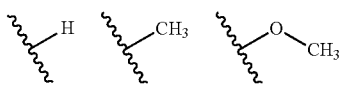

and $R_2$ is selected from:

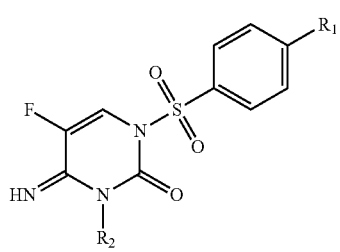

which comprises contacting compounds of Formula II with a base, such as an alkali carbonate, e.g., sodium-, potassium-, cesium-, and lithium carbonate ($Na_2CO_3$, $K_2CO_3$, $Cs_2CO_3$, and $Li_2CO_3$, respectively) or an alkali alkoxide, for example, potassium tert-butoxide ($KO^tBu$) and an alkylating agent, such as an alkyl halide of Formula $R_2$—X, wherein $R_2$ is as previously defined and X is a halogen, e.g., iodine, bromine, and chlorine, in a polar solvent, such as N,N-dimethylformamide (DMF), dimethylsulfoxide (DMSO), dimethylacetamide (DMA), N-methylpyrrolidone (NMP), acetonitrile ($CH_3CN$), and the like, at concentrations from about 0.1 molar (M) to about 3 M. In some embodiments, a molar ratio of compounds of Formula II to the base is from about 3:1 to about 1:1 and a molar ratio of compounds of Formula II to alkylating agent is from about 1:1 to about 3:1. In other embodiments, molar ratios of compounds of Formula II to the base and compounds of Formula II to the alkylating agent a about 2:1 and about 1:3, respectively, are used. In some embodiments, the reactions are conducted at temperatures between −78° C. and 90° C., and in other embodiments, the reactions are conducted between 22° C. and 60° C.

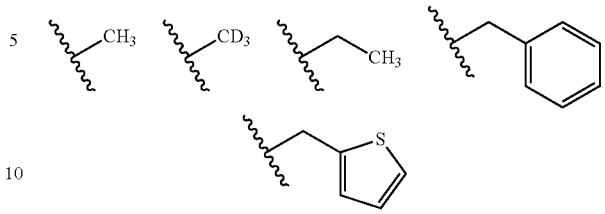

II

It will be understood by those skilled in the art that manipulation of the reaction parameters described above may result in the formation of product mixtures comprised of compounds of Formulas II, III, and IV, as shown in Scheme 1, wherein the ratios of compounds of Formulas II, III, and IV formed is from about 0:2:1 to about 1:2:0. In some embodiments, compositions comprising mixtures of compounds of Formulas II and III are preferred, as isolation and purification can be achieved through precipitation and recrystallization, and the intermediate compounds of Formula II can be recovered and recycled. In contrast, compositions comprising mixtures of compounds of Formulas III and IV require chromatographic separation to give III along with the undesired dialkylated by-product of Formula IV.

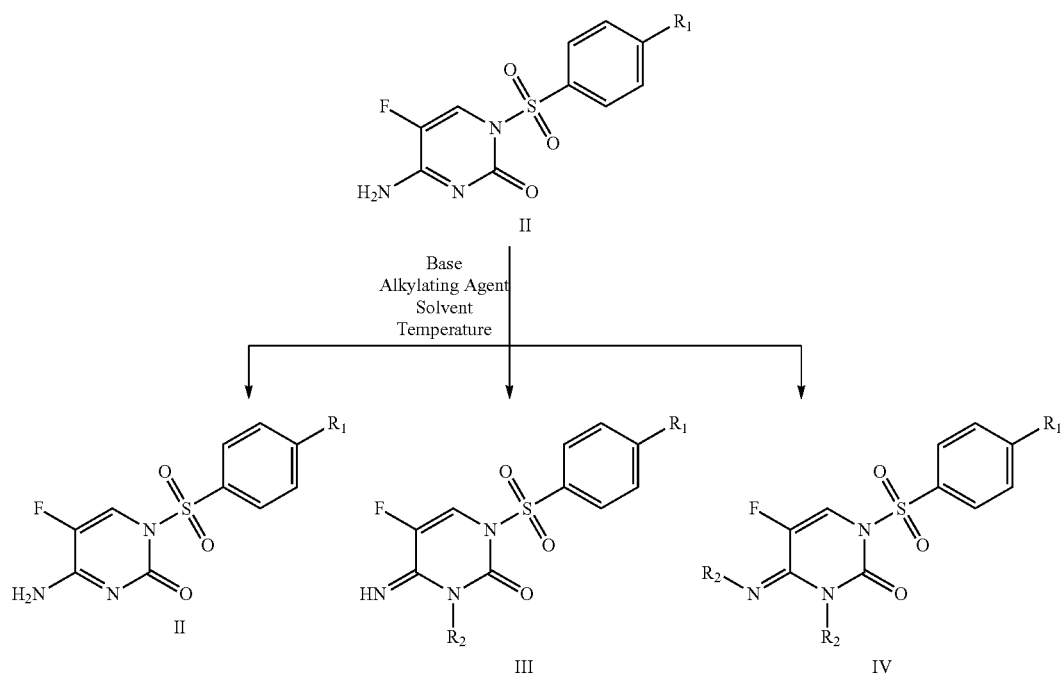

Scheme 1.

In another embodiment, the desired crude composition, i.e., mixtures of compounds of Formula II and compounds of Formula III, wherein $R_1$ is methoxy ($OCH_3$) and $R_2$ is methyl ($CH_3$), is obtained through contacting a compound of Formula II with $Li_2CO_3$ and methyl iodide ($CH_3I$) in DMF (1.0 M) in a molar ratio of about 1:0.6:3 at 45° C. Upon completion, dilution of the crude composition with a polar, aprotic solvent, such as $CH_3CN$, wherein the ratio of $CH_3CN$:DMF is from about 2:1 to about 1:2, followed by an aqueous solution of sodium thiosulfate ($Na_2S_2O_3$) with a pH from about 8 to about 10.5, wherein the ratio of 2.5 wt. % aqueous $Na_2S_2O_3$:DMF is from about 1:2 to about 3:1, affords a precipitate which is isolable by filtration. In one embodiment, the ratio of $CH_3CN$:DMF is about 1:2 and the ratio of 2.5% aqueous $Na_2S_2O_3$:DMF is about 1:1, and the resultant solid is further purified by crystallization/precipitation from a warmed solution, about 30° C.-40° C., of the solid h a solution of a polar, aprotic solvent, such as $CH_3CN$, by the addition of water ($H_2O$), wherein the ratio of $H_2O$:$CH_3CN$ is from about 1:2 to about 3:1, to give the purified compound of Formula III, and in another embodiment the ratio of $H_2O$:$CH_3CN$ to affect precipitation of pure III is about 2:1.

In another embodiment, compounds of Formula II may be prepared by contacting compounds of Formula I with bis-N,O-trimetliyisilylacetamide (BSA) at an elevated temperature, such as 70° C., for a period of about 1 hour (h), followed by cooling and contacting the solution containing the protected pyrimidinol with a substituted benzene sulfonyl chloride, generalized by $R_1$—$PhSO_2Cl$, wherein $R_1$ is as previously defined, at 20-25° C. In some embodiments, the molar ratio of the compound of Formula I to BSA and the sulfonyl chloride is about 1:3:1.1, respectively, and in another embodiment reducing the molar ratio of the reactants to about 1:1.1:1.1 affords improved yields.

I

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "aryl" refers to any aromatic, mono- or bi-cyclic, containing 0 heteroatoms.

The term "heterocycle" refers to any aromatic or non-aromatic ring, mono- or bi-cyclic, containing one or more heteroatoms.

The term "alkoxy" refers to an OR substituent.

The term "halogen" or "halo" refers to one or more halogen atoms, defined as F, Cl, Br, and I.

The term "haloalkyl" refers to an alkyl, which is substituted with Cl, F, I, or Br or any combination thereof.

Throughout the disclosure, references to the compounds of Formulas I, II, III, and IV are read as also including optical isomers and salts. Exemplary salts may include: hydrochloride, hydrobromide, hydroiodide, and the like. Additionally, the compounds of Formulas I, II, III, and IV may include tautomeric forms.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

In one exemplary embodiment, a method of making compounds of Formula III is provided. The method includes contacting a compound of Formula II with an alkali alkoxide and an alkylating agent, and forming a compound of Formula III:

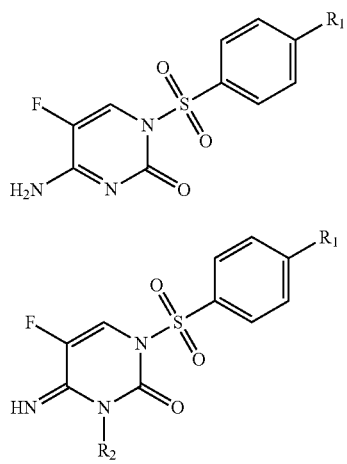

wherein $R_1$ is selected from the group consisting of:

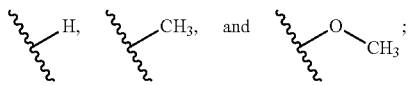

and $R_2$ is selected from the group consisting of:

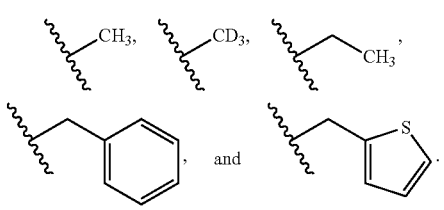

In a more particular embodiment, the contacting step is carried out between 22° C. and 60° C.

In a more particular embodiment of any of the above embodiments, the contacting step further includes a solvent selected from the group consisting of DMF, DMSO, DMA, NMP, and $CH_3CN$.

In a more particular embodiment of any of the above embodiments, the alkali alkoxide is selected from the group consisting of: $KO^tBu$, $CH_3ONa$, $CH_3CH_2ONa$, $CH_3CH_2OLi$, $CH_3OLi$, $CH_3CH_2OK$, and $CH3CH_2ONa$.

In a more particular embodiment of any of the above embodiments, the alkylating agent is selected from the group consisting of: alkyl halides and benzyl halides.

In a more particular embodiment of any of the above embodiments, the alkyl halide and benzyl halide are selected from methyl iodide ($CH_3I$), ethyl iodide ($C_2H_5I$), and benzyl bromide (BnBr).

In a more particular embodiment of any of the above embodiments, the alkali alkoxide is $KO^tBu$, and the solvent is DMF.

In a more particular embodiment of any of the above embodiments, a molar ratio of Compound II to alkali alkoxide is from about 3:1 to about 1:1 and a molar ratio of Compound II to alkylating agent is from about 1:1 to about 3:1. In an even more particular embodiment, a molar ratio of Compound II to alkali alkoxide base is about 2:1 a molar ratio of Compound II to alkylating agent is 1:3.

In a more particular embodiment of any of the above embodiments, the method includes diluting a completed reaction mixture with $CH_3CN$ and 2.5% aqueous $Na_2S_2O_3$. In an even more particular embodiment, a ratio of DMF to $CH_3CN$ is from about 1:1 to about 3:1 and a ratio of DMF to 2.5% aqueous $Na_2S_2O_3$ is from about 1:2 to about 2.1. In another more particular embodiment, a ratio of DMF to $CH_3CN$ is about 2:1 and a ratio of DMF to 2.5% aqueous $Na_2S_2O_3$ is about 1:1.

In another embodiment, a method of preparing a compound of Formula II is provided. The method includes contacting a compound of Formula I with bis-N,O-trimethylsilylacetamide; and forming a compound of Formula II

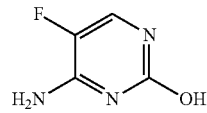

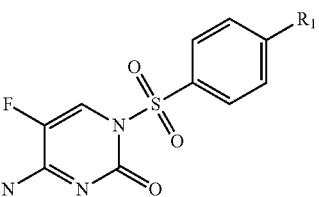

wherein $R_1$ is selected from the group consisting of:

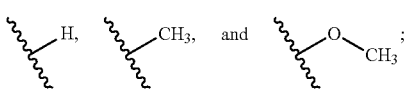

and $R_2$ is selected from the group consisting of:

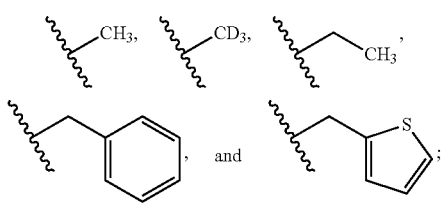

wherein a molar ratio of compound I to bis-N,O-trimethylsilylacetamide (BSA) is 1:1.1. and the contacting step is carried out at about 22° C. to about 70° C.

In a more particular embodiment, the contacting step further includes contacting compound I with $CH_3CN$. In another more particular embodiment, the method includes contacting a BSA treated reaction mixture with an arylsulfonyl chloride. In an even more particular embodiment, a molar ratio of Compound I to arylsulfonyl chloride is from about 1:2 to about 2:1, In another more particular embodiment, a molar ratio of Compound I to arylsulfonyl chloride is 1:1.1.

The embodiments described above are intended merely to be exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

DETAILED DESCRIPTION

5-Fluoro-4-imino-3-(alkyl/substituted alkyl)-1-(arylsulfonyl)-3,4-dihydro-pyrimidin-2(1H)-one as shown in Examples 1-2.

Example 1

Preparation of 4-amino-5-fluoro-1-(phenylsulfonyl)pyrimidin-2(1H)-one (1):

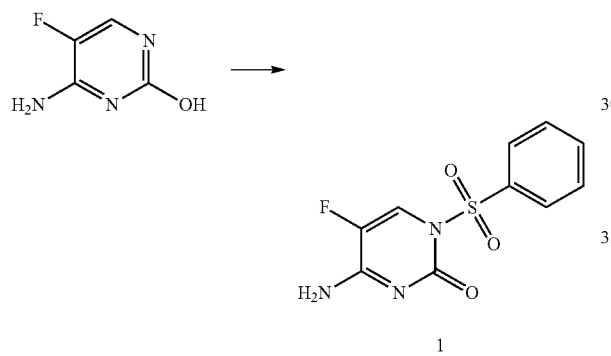

To a dry 500 milliliter (mL) round bottom flask equipped with a mechanical stirrer, nitrogen inlet, addition funnel, thermometer, and reflux condenser were added 5-fluorocytocine (20.0 grams (g), 155 millimole (mmol)) and $CH_3CN$ (100 mL). To the resulting mixture was added BSA (34.7 g, 170 mmol) in one portion and the reaction was warmed to 70° C. and stirred for 30 minutes (min). The resulting homogeneous solution was cooled to 5° C. with an ice bath and treated dropwise with benzenesulfonyl chloride. The reaction was stirred at 0° C.-5° C. for 1 h and then overnight at room temperature. The resulting pale yellow suspension was poured into cold $H_2O$ (1.5 liters (L)) and stirred vigorously for 1 h. The resulting solid was collected by vacuum filtration, washed with $H_2O$, and dried under vacuum overnight at 40° C. to give 4-amino-5-fluoro-1-(phenylsulfonyl)pyrimidin-2(1H)-one (29.9 g, 72%) as a powdery white solid: $^1$H NMR (400 MHz, DMSO-$d_6$) δ 8.56 (s, 1H), 8.35-8.26 (m, 2H), 8.07-7.98 (m. 2H), 7.84-7.74 (m, 1H), 7.72-7.61 (m, 2H); $^{19}$F NMR (376 MHz, DMSO-$d_6$) δ −163.46; ESIMS m/z 270 ([M+H]$^+$).

The following compounds 1-3 in Table 1a were made in accordance with the reaction depicted in Scheme 1 and the procedures described in Example 1. Characterization data for compounds 1-3 are shown in Table 1b.

Scheme 1.

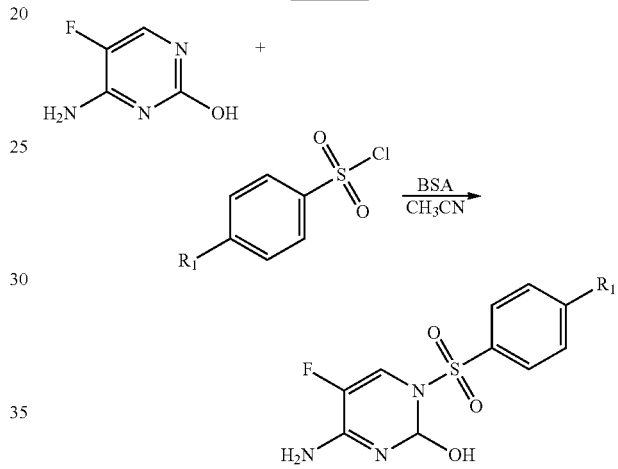

TABLE 1a

| Compound Number | $R_1$ | Appearance | Yield (%) |
|---|---|---|---|
| 1 | H | Powdery White Solid | 72 |
| 2 | $CH_3$ | Powdery White Solid | 61 |
| 3 | $OCH_3$ | Powdery White Solid | 57 |

TABLE 1b

| Compound Number | Mass Spec. | $^1$H NMR (δ)$^a$ | $^{13}$C NMR or $^{19}$F NMR (δ)$^{b,c}$ |
|---|---|---|---|
| 1 | ESIMS m/z 270 ([M + H]$^+$) | $^1$H NMR (DMSO-$d_6$) δ 8.56 (s, 1H), 8.35-8.26 (m, 2H), 8.07-7.98 (m, 2H), 7.84-7.74 (m, 1H), 7.72-7.61 (m, 2H) | $^{19}$F NMR (DMSO-$d_6$) δ −163.46 |
| 2 | ESIMS m/z 284 ([M + H]$^+$) | $^1$H NMR (DMSO-$d_6$) δ 8.54 (s, 1H), 8.40-8.16 (m, 2H), 8.05-7.76 (m, 2H), 7.66-7.36 (m, 2H), 2.41 (s, 3H) | $^{19}$F NMR (DMSO-$d_6$) δ −163.62 |

TABLE 1b-continued

| Compound Number | Mass Spec. | $^1$H NMR (δ)$^a$ | $^{13}$C NMR or $^{19}$F NMR (δ)$^{b,c}$ |
|---|---|---|---|
| 3 | ESIMS m/z 300 ([M + H]$^+$) | $^1$H NMR (CDCl$_3$) δ 8.10-7.91 (m, 2H), 7.73 (d, J = 5.4 Hz, 2H), 7.11-6.94 (m, 2H), 3.90 (s, 3H), 3.32 (d, J = 0.6 Hz, 3H) | $^{19}$F NMR (CDCl$_3$) δ −158.58 |

$^a$All $^1$H NMR data measured at 400 MHz unless otherwise noted.
$^b$All $^{13}$C NMR data measured at 101 MHz unless otherwise noted.
$^c$All $^{19}$F NMR data measured at 376 MHz unless otherwise noted.

Example 2

Preparation of 5-fluoro-4-imino-3-methyl-1-tosyl-3,4-dihydropyrimidin-2(1H)-one (5):

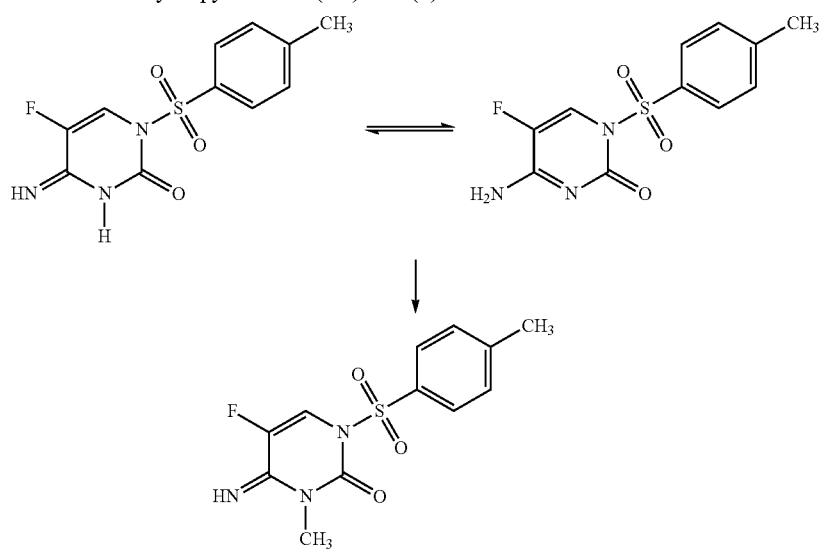

To a mixture of 4-amino-5-fluoro-1-tosylpyrimidin-2(1H)-one (20 mmol, 5.66 g) and Li$_2$CO$_3$ (0.880 g, 12.0 mmol) in DMF (20 mL) was added CH$_3$I (8.52 g, 60 mmol), and the resulting mixture was warmed to 40° C. and stirred for 5 h. The reaction mixture was cooled to room temperature, diluted with CH$_3$CN (10 mL), and treated with 2.5% aqueous Na$_2$S$_2$O$_3$ (20 mL). The resulting mixture was stirred at room temperature for 10 min and the solids were collected by filtration. The filter cake was washed with aqueous CH$_3$CN (10% CH$_3$CN in H$_2$O) and air dried for 2 h. The cake was dissolved in CH$_3$CN (15 mL) at 40° C. and the solution was treated with H$_2$O (30 mL). The resulting suspension was cooled to room temperature, stirred for 2.5 h, and filtered. The filter cake was again washed with 10% aqueous CH$_3$CN and then dried under vacuum at 50° C. to give the title compound (2.70 g, 45%) as a white solid: mp 156-158° C.; $^1$H NMR (400 MHz, DMSO-d$_6$) δ 8.54 (d, J=2.3 Hz, 1H), 7.99 (dd, J=6.0, 0.6 Hz, 1H), 7.95-7.89 (m, 2H), 7.53-7.45 (m, 2H), 3.12 (d, J=0.7 Hz, 3H), 2.42 (s, 3H); $^{19}$F NMR (376 MHz, DMSO-d$_6$) −157.86 (s); ESIMS m/z 298 ([M+H]$^+$).

The following compounds 4-6 in Table 2a were made in accordance with the reaction depicted in Scheme 2 and the procedures described in Example 2. Characterization data for compounds 4-6 are shown in Table 2b.

Scheme 2.

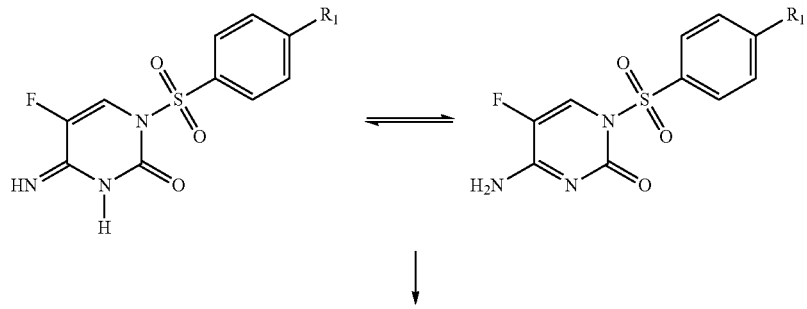

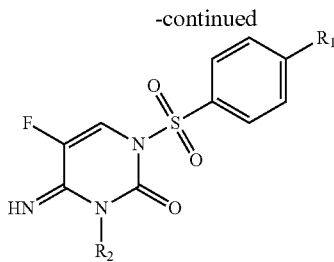

5

TABLE 2a

| Compound Number | $R_1$ | $R_2$ | Appearance | Yield (%) |
|---|---|---|---|---|
| 4 | H | $CH_3$ | White Solid | 64 |
| 5 | $CH_3$ | $CH_3$ | White Solid | 45 |
| 6 | $OCH_3$ | $CH_3$ | White Solid | 62 |

TABLE 2b

| Compound Number | Mass Spec. | $^1$H NMR (δ)$^a$ | $^{13}$C NMR or $^{19}$F NMR (δ)$^{b,c}$ |
|---|---|---|---|
| 4 | ESIMS m/z 284 ([M + H]$^+$) | $^1$H NMR (CDCl$_3$) δ 8.14-8.02 (m, 2H), 7.88-7.67 (m, 3H), 7.67-7.50 (m, 2H), 3.31 (d, J = 0.7 Hz, 3H) | $^{19}$F NMR (CDCl$_3$) δ −158.05 |
| 5 | ESIMS m/z 298 ([M + H]$^+$) | $^1$H NMR (CDCl$_3$) δ 8.54 (d, J = 2.3 Hz, 1H), 7.99 (dd, J = 6.0, 0.6 Hz, 1H), 7.95-7.89 (m, 2H), 7.53-7.45 (m, 2H), 3.12 (d, J = 0.7 Hz, 3H), 2.42 (s, 3H) | $^{19}$F NMR (CDCl$_3$) δ 157.86 (s) |
| 6 | ESIMS m/z 314 ([M + H]$^+$) | $^1$H NMR (CDCl$_3$) δ 8.10-7.91 (m, 2H), 7.73 (d, J = 5.4 Hz, 2H), 7.11-6.94 (m, 2H), 3.90 (s, 3H), 3.32 (d, J = 0.6 Hz, 3H) | $^{19}$F NMR (CDCl$_3$) δ −158.58 |

$^a$All $^1$H NMR data measured at 400 MHz unless otherwise noted.
$^b$All $^{13}$C NMR data measured at 101 MHz unless otherwise noted.
$^c$All $^{19}$F NMR data measured at 376 MHz unless otherwise noted.

What is claimed is:

1. A method of making compounds of Formula III, including the steps of:

contacting a compound of Formula II with an alkali alkoxide and an alkylating agent,

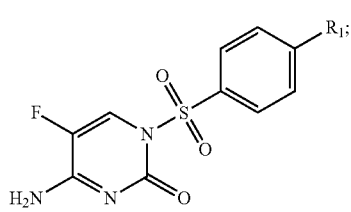

and
forming a compound of Formula III:

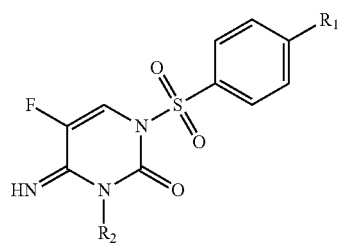

wherein $R_1$ is selected from the group consisting of:

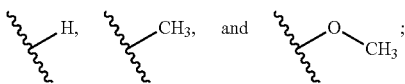

and
$R_2$ is selected from the group consisting of:

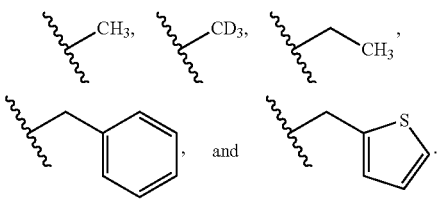

2. The method of claim 1, wherein the contacting step is carried out between 22° C. and 60° C.

3. The method of claim 1, wherein the contacting step further includes a solvent selected from the group consisting of: DMF, DMSO, DMA, NMP, and CH$_3$CN.

4. The method of claim 1, wherein the alkali alkoxide is selected from the group consisting of: KO$^t$Bu, CH$_3$ONa, CH$_3$CH$_2$ONa, CH$_3$CH$_2$OLi, CH$_3$OLi, CH$_3$CH$_2$OK, and CH$_3$CH$_2$ONa.

5. The method of claim 1, wherein the alkylating agent is selected from the group consisting of: alkyl halides and benzyl halides.

6. The method of claim 5, wherein the alkylating agent is an alkyl halide.

7. The method of any one of claims 3, 4, 5, or 6, wherein the alkali alkoxide is KO$^t$Bu, and the solvent is DMF.

8. The method of claim 7, wherein the molar ratio of the compound of Formula II to the alkali alkoxide is from about 3:1 to about 1:1 and the molar ratio of the compound of Formula II to the alkylating agent is from about 1:1 to about 3:1.

9. The method of claim 8, wherein a molar ratio of the compound of Formula II to alkali alkoxide is about 2:1 and a molar ratio of the compound of Formula II to alkylating agent is about 1:3.

10. The method of claim 9, further including the step of diluting a completed reaction mixture with CH$_3$CN and 2.5% aqueous Na$_2$S$_2$O$_3$.

11. The method of claim 10, wherein the ratio of DMF to CH$_3$CN is from about 1:1 to about 3:1 and the ratio of DMF to 2.5% aqueous Na$_2$S$_2$O$_3$ is from about 1:2 to about 2:1.

12. The method of claim 11, wherein the ratio of DMF to CH$_3$CN is about 2:1 and the ratio of DMF to 2.5% aqueous Na$_2$S$_2$O$_3$ is about 1:1.

13. The method of claim 2, wherein the contacting step is carried out between 22° C. and 45° C.

14. The method of claim 3, wherein the solvent selected from the group consisting of: DMF, DMA, and NMP.

15. The method of claim 6, wherein the alkyl halide is methyl iodide.

16. The method of claim 6, wherein the alkyl halide is ethyl iodide.

17. The method of claim 5, wherein the alkylating agent is a benzyl halide.

18. The method of claim 17, wherein the benzyl halide is benzyl bromide.

19. The method of claim 1, wherein R is

and R$_2$ is

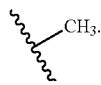

20. The method of claim 3, wherein the solvent is DMF.

* * * * *